United States Patent
Rice et al.

(10) Patent No.: US 9,238,117 B2
(45) Date of Patent: *Jan. 19, 2016

(54) INFORMATIVE ACCESSORIES

(75) Inventors: Caeli B. D. Rice, Monona, WI (US);
Jaron M. Acker, Madison, WI (US);
John E. Klaus, Cottage Grove, WI (US);
John R. Pinkert, Madison, WI (US)

(73) Assignee: General Electric Company,
Schenectady, NY (US)

( * ) Notice: Subject to any disclaimer, the term of this patent is extended or adjusted under 35 U.S.C. 154(b) by 1265 days.

This patent is subject to a terminal disclaimer.

(21) Appl. No.: 13/152,893

(22) Filed: Jun. 3, 2011

(65) Prior Publication Data

US 2011/0226249 A1    Sep. 22, 2011

Related U.S. Application Data

(63) Continuation of application No. 11/382,961, filed on May 12, 2006, now Pat. No. 7,980,245.

(51) Int. Cl.
| | |
|---|---|
| *F16K 31/02* | (2006.01) |
| *A62B 7/00* | (2006.01) |
| *A62B 9/00* | (2006.01) |
| *A61M 16/08* | (2006.01) |
| *G06Q 50/22* | (2012.01) |

(52) U.S. Cl.
CPC .............. *A61M 16/08* (2013.01); *G06Q 50/22* (2013.01); *A61M 16/0816* (2013.01); *A61M 2205/14* (2013.01)

(58) Field of Classification Search
CPC ............ A61M 16/08; A61M 16/0816; A61M 2205/14; A61M 2205/33; A61M 16/003
USPC ............. 128/204.18, 204.21, 204.23, 202.22, 128/205.23
See application file for complete search history.

(56) References Cited

U.S. PATENT DOCUMENTS

| | | | |
|---|---|---|---|
| 4,340,045 A | 7/1982 | Manley | |
| 5,069,220 A | 12/1991 | Casparie et al. | |
| 5,088,332 A | 2/1992 | Merilainen et al. | |
| 5,337,738 A | 8/1994 | Heinonen | |
| 5,950,621 A | 9/1999 | Klockseth et al. | |
| 6,035,851 A | 3/2000 | Wallen | |
| 6,089,105 A | 7/2000 | Ricciardelli | |
| 6,119,686 A | 9/2000 | Somerson et al. | |
| 7,101,341 B2 | 9/2006 | Tsukashima et al. | |
| 7,980,245 B2 * | 7/2011 | Rice ...................... | A61M 16/08 128/204.21 |
| 2003/0140921 A1 | 7/2003 | Smith et al. | |
| 2003/0196666 A1 | 10/2003 | Leonard | |
| 2004/0173214 A1 | 9/2004 | Tinker | |
| 2005/0038674 A1 | 2/2005 | Braig et al. | |
| 2007/0272240 A1 | 11/2007 | Aylsworth et al. | |

* cited by examiner

*Primary Examiner* — Kristen Matter

(74) *Attorney, Agent, or Firm* — Andrus Intellectual Property Law, LLP

(57) ABSTRACT

An optimized system for providing medical support to a patient is disclosed. The system has a plurality of modular components that may be assembled to create a connection between a support machine and the patient wherein at least one of the modular components comprises an information tag for the storage of data and at least one of the modular components comprises an information sensor for the reading and transmission of the data. Once read and transmitted by the sensor, the data may be used to optimize the operation of the support machine.

17 Claims, 3 Drawing Sheets

INFORMATIVE ACCESSORIES

CROSS REFERENCE TO RELATED APPLICATION

The present application is a continuation of U.S. patent application Ser. No. 11/382,961, filed May 12, 2006.

FIELD OF THE INVENTION

The present invention relates to the field of medical devices. More specifically, the invention relates to a system for ensuring the proper configuration of a medical device system comprising externally attached equipment.

BACKGROUND OF THE INVENTION

Many patients require respiratory support from a mechanical breathing system. A mechanical breathing system may be a ventilator for patients that need assistance breathing or it may be an anesthetic delivery device. A ventilator is connected to the patient via a series of specially designed modular components, each component being a tube. The ventilator applies a positive pressure to the airway of the patient. Once the natural resistance of the patient's airway is overcome by this positive pressure, the patient's lungs begin to fill with the supplied medical gases. The supplied medical gases may be air or may be a specific designated mixture of medical gases that provide some therapeutic support to the patient. This specific mixture of gases may include anesthetic agent or supplemental gases such as oxygen, helium, nitrogen, or nitrous oxide. During ventilatory support, it is desirable to monitor the flow of the medical gas within the ventilator system as well as the composition of the gas. This complex monitoring requires sophisticated mathematical models of the mechanical breathing system.

The mechanical breathing system has a plurality of modular components that may be linked together to create the connection between the ventilator and the patient. The use of disposable components increases sanitation by eliminating the need to sterilize medical components between uses. Alternatively, reusable components are available that must be sterilized between uses by a process such as autoclaving. Each modular component provides its own advantages and/or abilities and as such, the clinician can assemble the proper series of modular components for the patient's needs. For example, one such modular component may be a gas flow sensor/sampler, such as the D-lite available from GE Healthcare that has different models for use with adult and infant patients. As the clinician adds to or changes the modular components being used, the mathematical models used by the ventilator controls must be adjusted for the new components and the whole system optimized.

Similar challenges and concerns face clinicians in critical care situations where the patient is receiving an anesthetic agent. Anesthetic delivery machines comprise similar modular components creating the connection between the machine and the patient. Changing these components requires changing the mathematical models and optimizing the system controls.

Therapeutic error can result from the inattentive reconfiguration of a mechanical breathing system. System performance can be compromised when the operator fails to identify critical characteristics of modular components to the system prior to use. Normally, once the clinician has selected and assembled the necessary modular components, the clinician must tell a system controller which components are in use so that the controller knows the appropriate mathematical models to apply. Alternatively, the clinician must run a system "checkout" procedure by which a test flow is used to determine the characteristics of the mechanical breathing system. Running the checkout enables the system controller to get the resistance and compliance associated with the assembled breathing circuit. These parameters affect the system controller dynamics and alarm manager internal calculations. Significant negative effects are possible if the system assumes the incorrect parameters because the ventilation must be individually optimized for each patient's needs. Therefore, it is desirable for a system that automatically transfers detailed information about modular components to the controller for the mechanical breathing system with which the components are used.

An alternative problem facing clinicians of a critical care transport team is the need for a means to automatically transfer mechanical breathing system parameters and patient physiological trend information between mechanical breathing systems during transport. When transferring a critical care patient to a new location within the hospital, data pertaining to the patient's mechanical breathing system settings can be easily lost or it is time-consuming for the clinician to duplicate this data on the new mechanical breathing system. Therefore, it is desirable in the field of critical care transport to have a patient connection that stores data pertaining to the mechanical breathing system to be used when the patient is switched to a new mechanical breathing system.

SUMMARY OF THE INVENTION

The modular components of the present invention comprise an information tag comprising data that is associated with that modular component. The modular component further comprises an information sensor whereby information stored on an information tag may be transmitted to the controller of the mechanical breathing system.

In an embodiment of the present invention, the data associated with the information tag is data pertaining to the physical characteristics of the associated modular component.

In a further embodiment, the data associated with the information tag is such that it identifies the function of the associated modular component.

In a further embodiment of the present invention, the data associated with the information tag comprises the ability to be associated with patient data located on a centralized server.

In a still further embodiment of the present invention, the data associated with the information tag comprises information regarding the inventory and billing aspects of the associated modular component.

In a final embodiment of the present invention, the modular component comprises a plurality of modular components, each with an information tag and an information sensor, whereby the sensor of one modular component senses the information tag of another modular component and the data associated with the information tag is indicative of the connection between the two modular components.

DETAILED DESCRIPTION OF THE INVENTION

Figure 1:
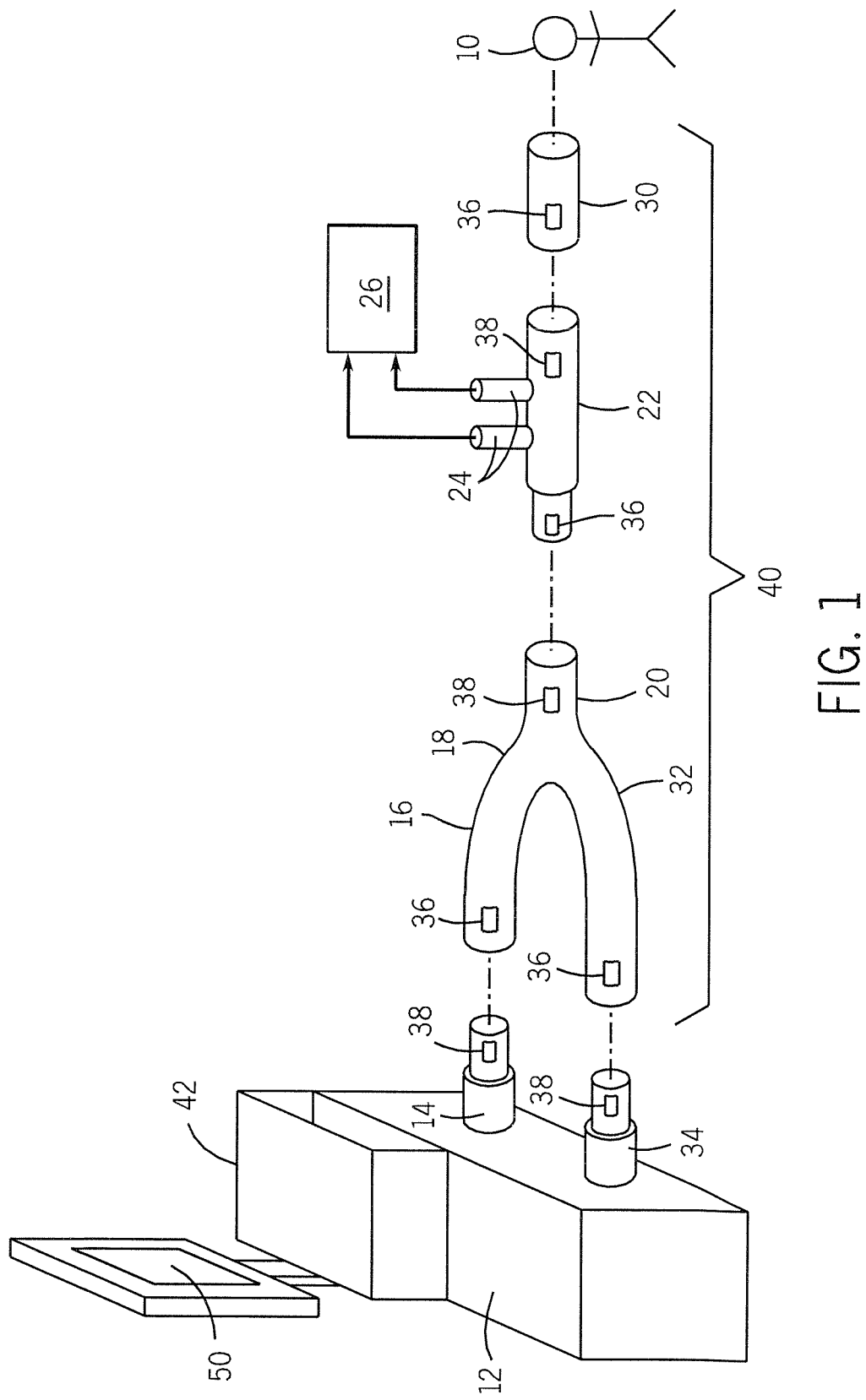
FIG. 1 is a schematic diagram depicting an embodiment of the present invention.

FIG. 1 is a schematic diagram depicting an embodiment of the present invention. Patient 10 is receiving an anesthetic agent from anesthesia delivery machine 12 controlled by a controller 42. The controller 42 ensures the proper mixture of medical gas is supplied to the patient 10 and facilitates the clinician's control over the anesthesia delivery machine 12 via a display 50 comprising a user interface (not pictured). It is understood that patient 10 could alternatively or additionally be in need of respiratory assistance to be supplied to the patient via a ventilator (not pictured). All descriptions of the present invention herein disclosed in regard to an anesthetic delivery system shall be interpreted to extend to ventilator systems as well as any other system capable of delivering medical gas to a patient.

The anesthesia delivery system 12 supplies medical gases to the patient 10 via a series of modular components 40. The anesthesia delivery system 12 applies a positive pressure of anesthetic medical gases through an inspiration valve 14 to the inspiratory limb 16 of a breathing circuit 18 and out the patient end 20 of the breathing circuit 18. The patient end 20 may be connected to a gas sampling module 22 that provides, via gas sampling ports 24, a sample of the gas provided to patient 10 to the spirometer/gas analyzer 26. Spirometer/gas analyzer 26, which may include the ability to measure gas concentration, pressure, and flow, may be a part of a larger general patient monitoring module (not pictured) for the monitoring of a wide variety of commonly monitored patient physiological parameters that are associated with the anesthetic delivery system 12. A patient connection 30, which may be a face mask, an endotracheal tube, nasal cannula, non-invasive helmet, or otherwise is connected at one end to the gas sampling module 22 and at the patient connection end facilitates the delivery of the medical gases to the patient 10. Gases expired by the patient 10 are returned to the anesthesia delivery system 12 via the breathing circuit 18, directed through the expiratory limb 32 and the expiratory valve 34.

While FIG. 1 depicts a setup or embodiment of an anesthetic delivery system that may be used in connection with the present invention, it is understood that alternative modular components 40 other than the aforementioned modular components 40 including: the breathing circuit 18, gas sampling module 22, and patient connection 30, may be used in delivering medical gases to the patient 10. Examples of such alternative modular components may include a gas humidifier or an external supply of a medical gas such as Nitrous Oxide (NO). The present description is meant to be exemplary and is not intended to be limiting on the configuration or types of modular components 40 as the modular components 40 may comprise any component known in the field to be disposed between a mechanical breathing system and a patient.

In an embodiment of the present invention, an information means, such as information tags 36, are placed on the modular components 40 of the anesthesia delivery system. As depicted in FIG. 1, for example, the breathing circuit 18 has an information tag 36 disposed at the ends of both the inspiratory limb 16 and expiratory limb 32. These information tags 36 may comprise radio frequency identification (RFID) technology; however, many types of information means may be used, including bar codes or infra-red technology. It is understood that any information means that is capable of retaining data or referring to stored data and having the data or reference read or transmitted would be within the scope of the present invention. The information tags 36 may be attached to the modular components 40 in any way that is feasible for the type of information tag 36 selected. In one embodiment, the information tags 36 are integrally attached to the modular components 40. In another embodiment, the information tags 36 are removably attachable to the modular components 40, allowing for use only as needed.

In an embodiment of the present invention depicted in FIG. 1, the information tags 36 would be read by information sensors 38 that are disposed on the modular components 40, or the anesthesia delivery system 12. As depicted in FIG. 1, information sensors 38 are disposed on the inspiration valve 14 and the expiration valve 34, respectively. The information sensors 38 are disposed in a way such that when the inspiratory limb 16 and expiratory limb 32 of the breathing circuit 18 are properly connected to the inspiration valve 14 and expiration valve 34 of the ventilator 12, the sensors 38 can read the data from the information tags 36 and this data is transmitted back to the controller 42 of anesthesia delivery system 12. It is understood that the information sensors 38 and the information tags 36 are selected to form compatible pairs such that the data stored in the information tags 36 is information that may be read by the information sensors 38. Furthermore, the transmission of the data by the information sensors 38 to the anesthetic delivery system 12 may comprise any suitable data transmission platform (not pictured) for use in a clinical setting. The platform may comprise wired or wireless data transmission platforms.

Figure 2:
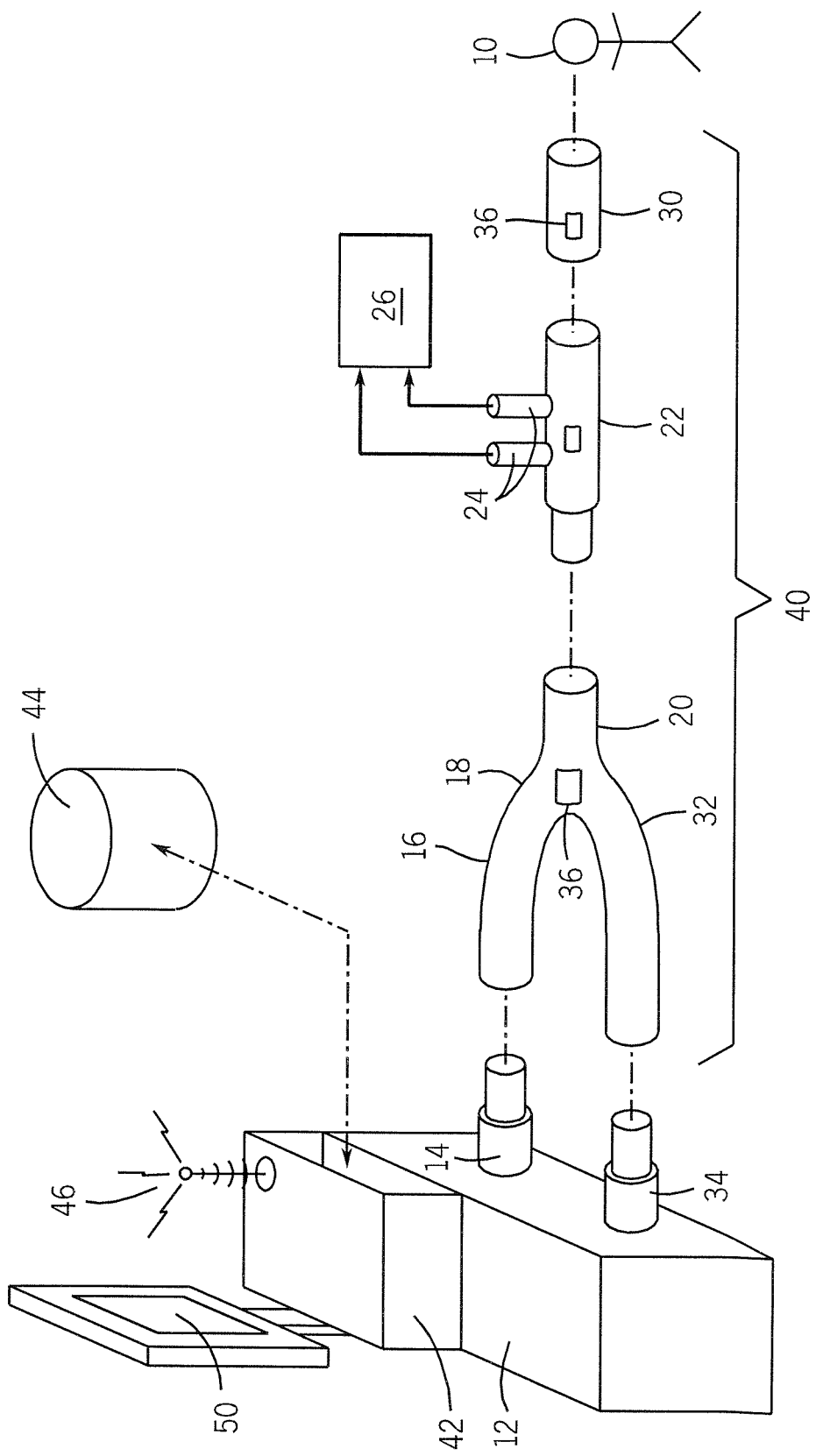
FIG. 2 is a schematic diagram depicting a further embodiment of the present invention.

An alternative embodiment depicted in FIG. 2 comprises information tags 36 that are associated with each of the modular components 40. In this embodiment comprising RFID information tags, the RFID tags may be short-range RFID tags with ranges less than ten meters that transmit a signal to the controller 42 of the anesthetic delivery system 12. A receiver 46, which in the embodiment depicted in FIG. 2 is an antenna, replaces the need for the individual information sensors 38 depicted in FIG. 1. The receiver 46 is associated with the controller 42 and detects the short-range RFID signals. This identifies the modular components 40 that are in close proximity to the anesthetic delivery system 12. These modular components 40 are presumably the ones that are connected to the anesthetic delivery system 12, and the controller 42 can modify the algorithms that it uses accordingly.

Figure 3:
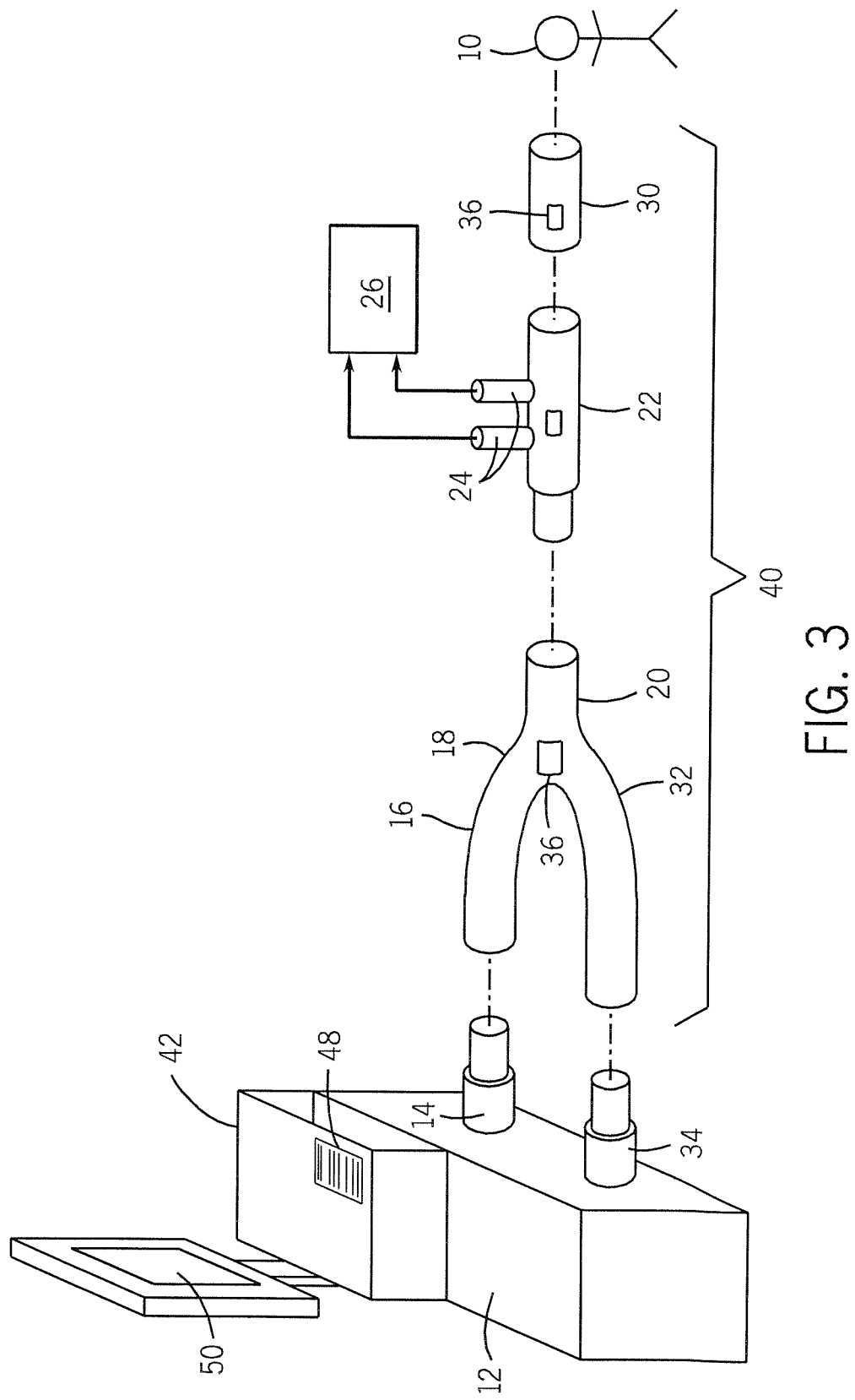
FIG. 3 is a schematic diagram depicting a further embodiment of the present invention.

An alternative embodiment depicted in FIG. 3 comprises information tags 36 that are associated with each of the modular components 40. This embodiment comprises information tags 36 such as bar codes or infra-red technology. In this embodiment a scanner 48 associated with the controller 42 replaces the information sensors 38 depicted in FIG. 1. As the clinician assembles the connection between the anesthetic delivery system 12 and the patient 10, the clinician scans each of the information tags 36 past the scanner 48. This identifies to the controller 42 the modular components 40 that are being assembled to complete the connection between the anesthesia delivery system 12 and the patient 10. The controller 42 can then modify the algorithms that it uses accordingly to reflect the modular components 40 that have been scanned.

Information tags 36 may comprise a wide variety of associated data to aid in improving many facets of the operation of the ventilator or anesthesia delivery systems 12. First, the information tags 36 may comprise calibration data. This data could provide information about the physical characteristics of the modular component 40 such as the resistance, size, or volume of the modular component 40. This information could also include valid operational ranges, internal alarm parameters, internal monitoring parameters and information that would aid in the automatic configuration and/or calibration of the system.

Information tags 36 may also comprise information regarding the specific modular component 40. This data may be especially important when the modular component 40 is a breathing circuit 18, gas sampling module 22 or a patient connection 30. For example, a gas sampling module 22 such as the D-lite, available from GE Healthcare, has one model to be used with adult patients (D-lite) and another to be used with infant patients (Pedi-lite). These models are specifically designed and calibrated for the different gas flows that are experienced in treating adults versus infants. Once selection of the proper D-lite module has been made, the clinician is typically required to indicate this to the controller 42 of the anesthetic delivery system 12. However, with this data present on the information tags 36 of the gas sampling module 22, this data can be automatically transmitted to the controller 42 of the anesthetic delivery system 12. In an alternate embodiment, if the modular component 40 is the patient connection 30, then data on the information tags 36 may comprise an indication of the type and model of the actual patient connection, whether it is a mask, an endotracheal tube, non-invasive ventilation helmet, or a nasal cannula. Regardless of the specific modular component 40 to which this embodiment is applied, it is necessary that the controller 42 of the anesthetic delivery system 12 be notified of the modular components 40 that are connected between the anesthesia delivery system 12 and the patient 10 so that the proper algorithms are used and calculations are made.

Embodiments of the present invention may comprise data associated with the information tags 36 that represents additional software that is required by the controller 42 of the anesthesia delivery system 12 for proper operation of the modular component and or the proper operation of the anesthesia delivery system 12 with respect to the modular component 40. This allows for new modular components 40 to be developed with additional software requirements without having to update the entire ventilator software. Alternatively, the data associated with the information tags 36 may comprise data that is used by the controller 42 to modify a user parameter of the controller. These user parameters may modify the user interface, or internal alarm parameters. This embodiment would allow for the user interface to change in its display of information to the clinician with regard to the modular components 40 that have been connected to the anesthesia delivery system 12. It would also allow for the modification of the alarm conditions with respect to the selected modular components 40.

In another embodiment of the present invention, the data associated with the information tag 36 comprises data for inventory control and/or billing management by the hospital. This data may comprise identification and stock numbers of the modular components 40, cost information, and/or patient information. This aspect of the invention will help to improve the hospital's ability to keep track of where hospital resources and medical supply inventory are used so that compensation may be received from the proper parties.

In a still further aspect of the present invention, the data associated with the information tags 36 on the modular component 40 may comprise patient data. This patient data may aid clinicians in critical care situations where a patient receiving respiratory or anesthetic support must be transferred to an alternative location with a new support machine. The data stored in the information tag 36 could comprise patient information regarding the setup of a first support machine so that a second support machine may be similarly configured upon connection to the patient 10. The data associated with the information tag 36 may also refer to patient data stored at a remote location such that the second support machine may have access to patient history information. This allows the second support machine to utilize more complex algorithms for the trending and patient response of physiological parameters that require the additional patient information.

An alternative embodiment further depicted in FIG. 2 comprises the information tags 36 that are associated with each of the modular components 40. However, in this embodiment, the information tags 36 only comprise data that references or identifies remotely located associated data. This remotely located data may be located at a centralized hospital server 44. Upon receiving the data on the information tags 36, the controller 42 uses that reference data to access the desired data on the centralized server 44. In this embodiment, complex data may be stored at the centralized server 44 which would have a much greater data storing capacity. The data stored in the centralized server 44 may comprise data such as the modular component 40 characteristic data, anesthetic delivery system 12 configuration data, or data that is associated with the patient being treated such as patient history, or other recorded physiological data. The advantage of this embodiment is that it simplifies the information tag 36 needed by reducing the amount of data that it comprises.

In a final embodiment of the present invention, a system of modular components 40, as in FIG. 1, are connected together to provide the connection between the anesthetic delivery system 12 and the patient 10. Each modular component 40 has at least one information tag 36 and one information sensor 38 such that each place that two modular components 40 connect sensor 38 are from one modular component 40 can read the data from the information tag 36 of the other modular component 40. The data from the information tag 36 is data that is indicative of a proper connection between the two modular components 40. Once detected, this data is sent from the sensor 38 to the controller 42 indicating that a connection has been made. Thus, the anesthesia controller 42 can automatically determine if the modular components 40 have been properly connected to each other. Additionally, the controller 42 can monitor the connection of the modular components 40 throughout the treatment of the patient, raising an alarm if a modular component 40 becomes disconnected. Improperly connected modular components 40 can produce, at best, inaccurate data and waste of medical gases, and at worst, a dangerous situation for patients and clinicians alike. This embodiment promotes safety and efficiency in the assembly of modular components 40 to be used in conjunction with a ventilator or anesthesia delivery system 12 by protecting against clinician error.

The controller 42 of the anesthetic delivery system 12 in this embodiment may have the ability to also control a display 50 associated with the anesthetic delivery system 12. The controller 42 may direct the display 50 to display a visual representation of the detected modular components 40 forming the connection between the anesthetic delivery system 12 and the patient 10. This visual representation would serve to inform a clinician as to the current configuration of modular components 40 that the anesthesia delivery system 12 and controller 42 are operating under. The visual representation would allow the clinician to quickly confirm that the configuration indicated to the controller 42 is the configuration that is actually present.

The advantage of this invention is that it improves the operation of a ventilator or anesthesia delivery machine 12 by eliminating sources of human error during reconfiguration of the breathing system and lab data acquisition. The present invention provides an efficient and accurate anesthetic or ventilation system as the present invention optimizes many aspects such as the control system, monitoring system, and alarm manager. The present invention further optimizes the anesthetic delivery or ventilation system 12 by eliminating the need to run system configuration or "checkout" procedures before care is delivered to the patient and ensuring the proper connection of the modular components 40. This reduces the time that it takes for the clinician to begin providing medical care to the patient.

This written description uses examples to disclose the invention, including the best mode, and also to enable any person skilled in the art to make and use the invention. The patentable scope of the invention is defined by the claims and may include other examples that occur to those skilled in the art. Such other examples are intended to be within the scope of the claims if they have structural elements that do not differ from the literal language of the claims, or if they include equivalent structural elements of insubstantial difference from the literal language of the claims.

Various alternatives and embodiments are contemplated as being with in the scope of the following claims, particularly pointing out and distinctly claiming the subject matter regarded as the invention.

We claim:

1. A system for providing support for a patient, the system comprising:
    a mechanical ventilator that generates a flow of medical gas to be delivered to the patient;
    a controller that operates using a plurality of controller data, wherein the controller is communicatively connected to the mechanical ventilator and operates the mechanical ventilator;
    a plurality of modular components, the plurality of modular components being interconnected to establish a fluid connection between the mechanical ventilator and the patient;
    at least one information tag associated with each of the modular components and the at least one information tag comprises associated data that is used by the controller to modify the controller data, which modifies the operation of the controller; and
    at least one tag sensor that detects the associated data from the plurality of tags and transmits the detected associated data to the controller;
    wherein the controller receives the associated data, modifies the controller data, and modifies the operation of the controller.

2. The system of claim 1, wherein the associated data identifies the modular component.

3. The system of claim 2, wherein the controller uses the identification of the modular component for billing and inventory control operations.

4. The system of claim 2, wherein the controller uses the identification of the modular component to provide a notification of the modular components in the plurality of modular components.

5. The system of claim 1, wherein the associated data is patient physiological data stored on the at least one information tag, and the controller uses the patient physiological data to operate the mechanical ventilator.

6. The system of claim 5, wherein the controller is a stand-alone controller, and the at least one tag sensor is an input device for the input of patient physiological data.

7. The system of claim 1, wherein the associated data is software, and the controller installs the software from the at least one information tag and operates the software.

8. The system of claim 1, further comprising:
    a graphical display that is communicatively connected to the controller and operated by the controller;
    wherein the associated data are user parameters, and the controller operates the graphical display according to the user parameters.

9. The system of claim 1, wherein the associated data is an alarm parameter specific to the modular component, and the controller operates to monitor the alarm parameter specific to the modular component.

10. The system of claim 1, wherein the mechanical ventilator is a first mechanical ventilator and the controller is a first controller, the system further comprising:
    a second mechanical ventilator that generates a flow of medical gas to be delivered to the patient; and
    a second controller that operates using a plurality of controller data, wherein the controller is communicatively connected to the mechanical ventilator and operates the mechanical ventilator;
    wherein the plurality of modular components are initially connected to the first mechanical ventilator, and the first controller operates according to the associated data; and
    wherein the plurality of modular components are disconnected from the first mechanical ventilator and reconnected to the second mechanical ventilator and the second controller operates the same as the first controller according to the associated data.

11. A system for providing support for a patient, the system comprising:
    a mechanical ventilator that generates a flow of medical gas to the patient;
    a controller connected to the ventilator that operates the mechanical ventilator;
    a server communicatively connected to the controller, wherein the server stores a plurality of associated data;
    a plurality of modular components, the plurality of modular components interconnected to establish a fluid connection between the mechanical ventilator and the patient;
    at least one information tag associated with each of the modular components and the at least one information tag comprises reference data that identifies an associated data stored on the server; and
    at least one tag sensor that detects the reference data from the plurality of tags and transmits the detected reference data to the controller;
    wherein the controller receives the reference data from the at least one tag sensor, and uses the received reference data to acquire the associated data for modifying the operation of the ventilator and the controller modifies operation of the ventilator to be specific to each of the modular components.

12. The system of claim 11, wherein the associated data is patient physiological data stored on the server, and the controller uses the patient physiological data to operate the mechanical ventilator.

13. The system of claim 12, wherein the associated data is the patient physiological data in a patient electronic medical record stored on the server.

14. The system of claim 11, wherein the associated data is software, and the controller installs the software from the server and operates the software.

15. The system of claim 11, further comprising:
    a graphical display that is communicatively connected to the controller and operated by the controller;
    wherein the associated data are user parameters, and the controller operates the graphical display according to the user parameters.

16. The system of claim 11, wherein the associated data is an alarm parameter specific to the modular component, and the controller operates to monitor the alarm parameter specific to the modular component.

17. The system of claim 11, wherein the mechanical ventilator is a first mechanical ventilator and the controller is a first controller, the system further comprising:
   a second mechanical ventilator that generates a flow of medical gas to be delivered to the patient; and
   a second controller that operates using a plurality of controller data, wherein the controller is communicatively connected to the mechanical ventilator and operates the mechanical ventilator;
   wherein the plurality of modular components are initially connected to the first mechanical ventilator, and the first controller operates according to the associated data; and
   wherein the plurality of modular components are disconnected from the first mechanical ventilator and reconnected to the second mechanical ventilator and the second controller operates the same as the first controller according to the associated data.

* * * * *